US005957423A

United States Patent [19]
Kronner

[11] Patent Number: 5,957,423
[45] Date of Patent: Sep. 28, 1999

[54] LOW PROFILE SCOPE HOLDER

[76] Inventor: Richard F. Kronner, 1443 Upper Cleveland Rapids Rd., Roseburg, Oreg. 97470

[21] Appl. No.: 08/964,729

[22] Filed: Nov. 5, 1997

[51] Int. Cl.[6] .................................................. A61B 17/00
[52] U.S. Cl. ...................................... 248/278.1; 600/228
[58] Field of Search ........................... 248/278.1, 299.1, 248/274.1, 279.1; 600/102, 228, 229

[56] References Cited

U.S. PATENT DOCUMENTS

| | | | |
|---|---|---|---|
| 114,243 | 4/1871 | Wood et al. | 248/278.1 |
| 373,362 | 11/1887 | Hamilton | 600/234 |
| 1,084,427 | 1/1914 | Hanks | 248/103 |
| 1,403,863 | 1/1922 | Peat | 248/219.4 |
| 4,170,336 | 10/1979 | Malis | 248/279.1 |
| 4,355,631 | 10/1982 | LeVahn | 600/230 |
| 4,573,452 | 3/1986 | Greenberg | 600/102 |
| 4,617,916 | 10/1986 | LeVahn et al. | 600/228 |
| 4,863,133 | 9/1989 | Bonnell | 248/280.11 |
| 4,867,404 | 9/1989 | Harrington et al. | 248/231.4 |
| 5,104,103 | 4/1992 | Auchinleck et al. | 269/74 |
| 5,205,522 | 4/1993 | Nakamura | 248/123.11 |
| 5,224,680 | 7/1993 | Greenstein et al. | 248/316.4 |
| 5,284,130 | 2/1994 | Ratliff | 600/229 |
| 5,383,637 | 1/1995 | Biber | 248/291.1 |
| 5,441,042 | 8/1995 | Putnam | 600/102 |
| 5,571,072 | 11/1996 | Kronner | 600/102 |
| 5,824,007 | 10/1998 | Faraz et al. | 600/130 |

OTHER PUBLICATIONS

Stoney, Ronald J., MD, "How to Achieve Optimum Exposure of the Upper Abdominal Aorta and its Branche", Minnesota Scientific, Dec. 1986, pp. 1–4.

Computer Motion, Inc., Goleta, California, "Enhancing Performance through Robotics" and Robotic Enhancement Technology, 1 sheet.

Leonard Medical, Inc., Huntingdon Valley, Pennsylvania—literature on the Leonard Arm, Leonard Arm Jr., Laparoscope Holder and Instrument Holder, Oct. 20, 1993,—11 pages.

Omni–Tract Surgical, St. Paul, Minnesota—literature on Corral Retractor, Omni–Lapotract System and Omni–Tract Accessories, 1991 and 1993, 4 sheets.

Computer Motion, Inc., Goleta, California,"AESOP: Automated Endoscopic System for Optimal Positioning", undated, 4 pages.

Cuschieri, Alfred, M.D., "Minimal Access Surgery and the Future of Interventional Laparoscopy", The American Journal of Surgery, vol. 161, Mar. 1991, pp. 404–407.

Omni–Tract Surgical Catalog featuring System Components, Retractors, Blades and Accessories, 1991—8 pages.

NASA Tech Briefs, "Robotics for Safer Surgery", Jan. 1994, vol. 18, No. 1, pp. 16–18.

Nathanson et al., "Laparoscopic Cholecystectomy", Br. J. Surg., vol. 78, No. 2, Feb. 1991, p. 155.

Omni–Tract Surgical a Divison of Minnesota Schientific, Inc., St. Paul, MN—Literature on the Stoney Mini–Vascular Retractor System—VM100, Nov. 1991, 4 pages.

The Iron Intern Robotic Retractor, Your Most Dependable Assistant—1 sheet with photograph of same,.

Berci et al., "New Ideas and Improved Instrumentation for Laparoscopic Cholecystectomy", Surgical Endoscopy, vol. 5, 1991, pp. 1 and 3.

ELMED Inc., Addison, Illinois—literature on the ELMED Endoscopic Fixation Device, 4 pages.

*Primary Examiner*—Ramon O. Ramirez
*Assistant Examiner*—Anita M. King
*Attorney, Agent, or Firm*—Anderson & Adamson; C. Douglas DeFreytas

[57] ABSTRACT

An endoscope holder includes a dual-axis pivot assembly mountable to a frame. A telescoping arm assembly is attached at one end to the dual-axis pivot assembly and at the other end to a pivoting endoscope grip. An inner arm section is rotatable relative to an outer arm section. The holder provides pivoting of an endoscope about an incision point on the endoscope shaft spaced from the grip. Manually controlled pressurized locks secure the holder configuration, and thereby the endoscope position.

15 Claims, 12 Drawing Sheets

LOW PROFILE SCOPE HOLDER

BACKGROUND OF THE INVENTION

1. Field of the Invention

This invention relates to structure for supporting a surgical instrument, such as a laparoscope, and more particularly to a low profile structure which provides for repositioning of the instrument during surgery without stressing an incision through which the instrument extends.

2. Related Art

Laparoscopic surgery is a procedure in which surgical instruments and a viewing scope, referred to generally as an endoscope and more specifically as a laparoscope, are inserted through respective small puncture wounds or incisions into the abdominal cavity of a patient. A small video camera is attached to the laparoscope and connected to a television monitor for viewing the procedure.

The instruments and the laparoscope are inserted through cannulae which are first inserted through the incisions. Cannulae are hollow tubes with gas valves. The cannulae are left in the puncture wounds throughout the procedure. The cannulae allow the instruments and scope to be removed and reinserted as necessary.

To aid in visualizing the intraabdominal structures, gas is inserted through one of the cannulae to raise the abdominal wall. Seals are required at the exit points of the scope and instruments to prevent the gas from escaping.

The viewing laparoscope is inserted through a cannula which is usually inserted through an incision made in the umbilicus. The scope is then directed toward the pelvis for pelvic surgery or toward the liver for gallbladder surgery.

Throughout the procedure it is necessary for the surgeon, assistant surgeon, or a scrub nurse to hold the scope and direct it at the target of the surgery. It is constantly being repositioned to obtain the best view. This process ties up one hand of the surgeon or assistant surgeon, if either holds the scope. The scrub nurses also have other tasks to perform, and holding the scope interferes with performing these tasks. It is also difficult for the surgeon to direct others to position the scope for the best view. As a result, when the scope is not held by the surgeon, it is often misdirected.

The support of a laparoscope has been provided through the use of robotic retractors. Retractors hold instruments in fixed positions, such as for holding an incision open to allow a surgeon access to the underlying body parts. The retractors are fixedly clamped to a mechanical skeleton. This skeleton has also been used to hold a laparoscope in a fixed position. When it is desired to move the scope, the clamp must be readjusted, and also the skeleton linkages must usually also be adjusted to accommodate a change in angle of insertion of the laparoscope.

An apparatus that accommodates changes more readily is a robot-like arm having ball joints next to an instrument holder. This apparatus is sold under the proprietary name, The Leonard Arm, by Leonard Medical, Inc. of Huntingdon Valley, Pa., and is described in U.S. Pat. No. 4,863,133 issued to Bonnell. Two articulating arms are used to couple an instrument clamp to the operating table rail. A vacuum supply is used to frictionally hold the joints. Three joints provide three degrees of freedom of movement. When not freely moveable, manual force on the instrument clamp is sufficient to reposition the instrument.

The invention of Bonnell is intended as a general-purpose instrument holding apparatus. As such it is up to the user to control movement of the instrument supported on the apparatus, since the axes of movement are independent of and spaced from the patient, except for ball joints next to the instrument holder. Further, this apparatus presents two arms that extend upwardly over the operating table which interfere with access to the patient by attendants, and requires a dedicated vacuum source in the operating room.

A less imposing and more technically sophisticated robotic arm that is commercially available is sold under the name, AESOP, by Computer Motion, Inc. of Goleta, Calif. This arm has servo-operated joints with computer-controlled motion based on a multipedal foot-operated input device. This device has articulation on about axes that are also spaced from the endoscope, thereby requiring very careful movement control by the surgeon in order to avoid stressing the tissue adjacent the laparoscope incision. Further, the computer used to control movement makes the system very expensive to produce.

A less expensive manual apparatus is described in U.S. Pat. No. 4,573,452 issued to Greenberg. A rigid metal ring that surrounds the incision area is mounted above the table. A vertical control arm is mounted on a ball-and-socket joint along the metal ring. A tensionable cable-like component connects the top of the control arm to a laparoscope holder. After initial placement of the holder, the cable-like component is secured, after which movement of the laparoscope is achieved by pivoting the control arm about the ball and socket joint. It is suggested that the ball and socket joint be coplanar with the incision through which the laparoscope extends.

The Greenberg apparatus requires the use of the ring which is positioned over the patient. This ring, though of low profile, can interfere with surgical procedures. Further, the laparoscope is pivoted about the ball-and-socket joint which is located along the ring. Thus, except for movement of the scope about the axis that intersects both the incision and joint, the laparoscope moves from the incision, causing stress on the tissue around the incision. A significant change in position of the scope requires release and repositioning of the cable-like component.

SUMMARY OF THE INVENTION

The present invention overcomes disadvantages of these prior art devices. Generally, the present invention provides an endoscope holder apparatus that provides for adjustment of the endoscope, once it is positioned through an incision, without stressing the tissue surrounding the incision. This invention further provides a low-profile holder that avoids interference with other instruments or the surgical team during a surgical procedure. The invention also provides for one-hand operation such that the surgeon may unlock and reposition the laparoscope with only one hand; thereafter, operation is hands-free until repositioning is required.

More specifically, the present invention provides a laparoscope holder apparatus having a base fixedly mountable on an external frame, such as a surgical table. A grip which holds the laparoscope is pivotally mounted at the end of a telescoping arm assembly permitting rotational and longitudinal placement of the grip. The arm assembly is pivotally mounted relative to the base and further is preferably movable through an arc in a vertical plane which is parallel to a vertical pivotal axis.

The preferred embodiment of the invention includes a base clamp assembly fixedly mountable at a position along a mounting rail of a surgical table. The base clamp assembly fixedly secures a keyed shank in a selected vertical position and in a selected orientation about a vertical axis. A first pivot assembly secures a first pressurized gas operable friction pivot assembly atop the keyed shank for pivoting the arm assembly about the vertical axis and through an arc in a horizontal axis. An arm clamp fixedly secures a first section of the arm in a selected position along a longitudinal axis. A second section of the arm telescopes from the first section of the arm along the longitudinal axis and is rotatable about the longitudinal axis through a pressurized gas operable friction lock assembly attached to the arm clamp.

A grip is fixedly mountable to an endoscope for holding the endoscope along a scope axis that intersects the longitudinal axis at a pivot point. Finally, a second manually operable friction pivot joint is mounted on an end of the second section of the arm. The second pivot joint is attached to the grip for pivoting the grip relative to the second section of the arm about a grip pivot axis that is orthogonal to and intersects the longitudinal axis at the pivot point.

The pressurized gas operable friction pivots and lock assembly are locked by pressurized gas through a switch that is normally open. When the switch is operated, the pressurized gas is blocked from the source and vented from the friction joints and lock assembly. Sufficient friction exists to prevent the apparatus from collapsing when the switch is off, but in the switch off position, the endoscope may be adjusted about the vertical, horizontal, and longitudinal axes, and along the longitudinal axis to a new position. An endoscope is thereby moveable in a cone-shaped region by pivoting about an incision point on the axis of the scope shaft. Upon release of the switch, the apparatus is locked in the new position.

These and other features and advantages of the present invention will be apparent from the preferred embodiment described in the following detailed description and illustrated in the accompanying drawings.

DETAILED DESCRIPTION OF THE PREFERRED EMBODIMENT

Figure 1:
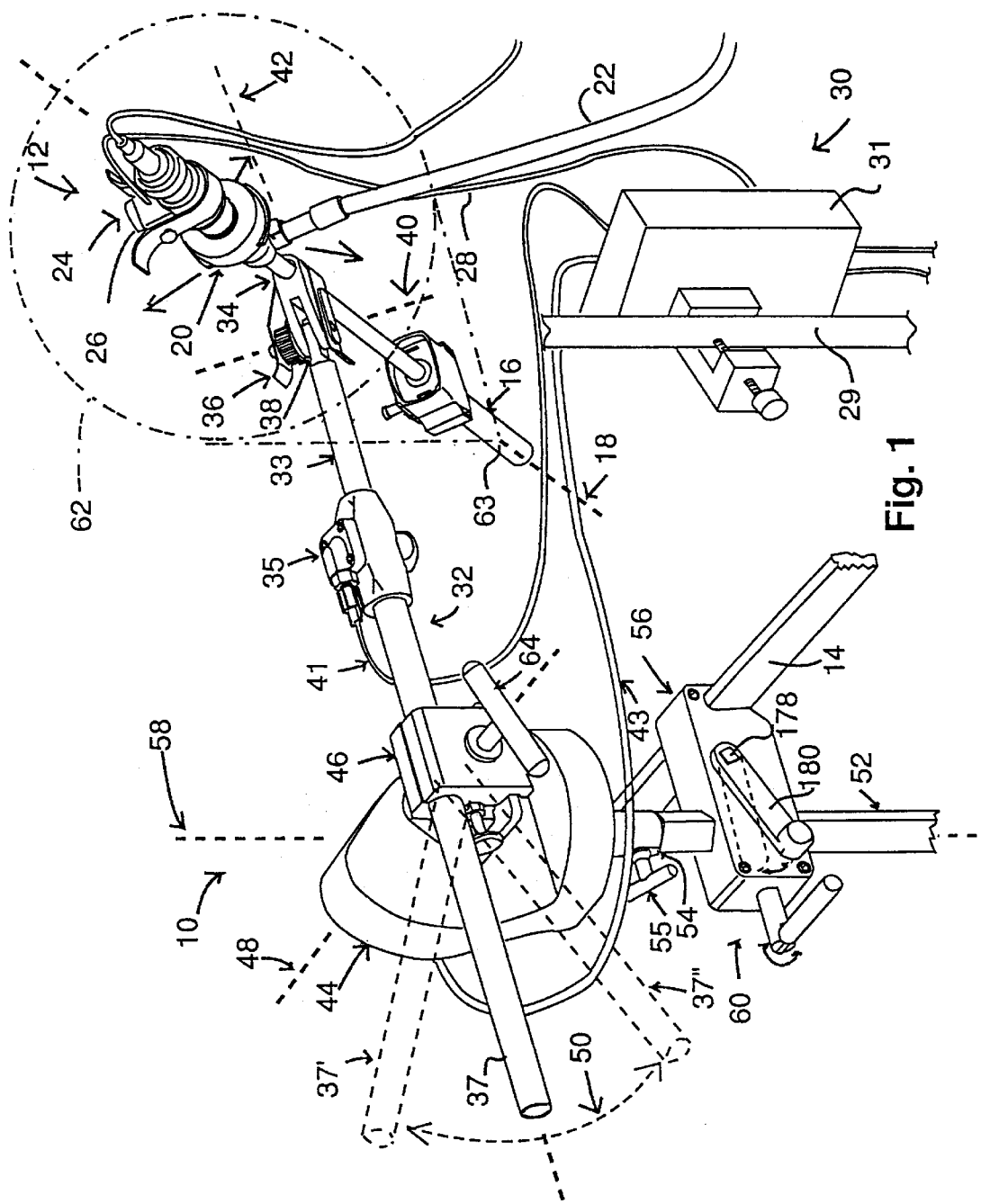
FIG. 1 is an isometric view of an apparatus made according to the invention.

Referring initially to FIG. 1, an apparatus 10 is shown for supporting a conventional endoscope 12 relative to an operating table having an equipment mounting rail 14. The term endoscope as used herein also refers to associated equipment, such as a cannula 16. The tubular end of the cannula extends along a support axis 18 coincident with what is also referred to as a shaft axis. Although reference is made specifically to an endoscope, the invention may also be used to support other instruments as well.

The endoscope includes a camera 20 with its attached light line 22 connected to remote monitoring equipment. Also attached to cannula 16 is a control switch 24 with a button 26, and an electrical control line 28. Control switch 24 is part of a lock control system 30 having further components housed in a housing 31 mounted to a support pole 29, such as the type used for intravenous fluid administration. Cannula 16 is attached to a telescoping arm assembly 32 at distal arm section 33 by grip 34 using a resilient strap 36. A lock assembly 35 provides a transition between a proximal arm section 37 and arm section 33. A first gas outflow line 41 feeds pressurized gas to lock assembly 35. A second gas outflow line 43 feeds a lock assembly in a first pivot assembly 44, described below.

A grip 34 forms a second pivot assembly 38 which permits grip 34 to pivot about a grip axis 40. Arm section 33 is extendable from arm section 37 along longitudinal axis 42. Arm section 37 is mounted to first pivot assembly 44 with a fourth clamp assembly 46. Clamp assembly 46 permits arm assembly 32 to pivot through an arc 50 about a horizontal axis 48. For clarity the travel of arm assembly 32 through arc 50 is shown only at one end of arm assembly 32. It should be understood that the entire arm assembly 32, including arm section 33 travels through arc 50.

First pivot assembly 44 is mounted atop a keyed shank 52 by a third clamp assembly 54 having a handle 55. Shank 52 is matingly insertable in a base 56. In the embodiment shown, the keyed shank and mating keyway in base 56 are square, permitting any of four possible mounting orientations about a vertical axis 58. It can be visualized that shank 52 and the mating keyway in base 56 could be constructed in other geometric patterns permitting a different number of mounting orientations. A base clamp assembly 60 secures shank 52 at any desired height along axis 58 providing a multiplicity of height settings for first pivot assembly 44. Clamp assembly 60 also provides for attachment of the apparatus to mounting rail 14. Base clamp assembly 60 is shown in further detail in FIGS. 13 and 14.

Through the articulation provided by pivot axes 40, 48, 50 and telescoping arm axis 42, endoscope 12 may be moved in a relatively large cone-shaped region, represented by dash-dot circle 62, about a single point 63 on support axis 18 spaced from grip 34. Axis 18, which corresponds to the longitudinal axis of the endoscope, passes through an incision during use. Point 63 is selected by the user and preferably corresponds to the point where the endoscope shaft passes through an incision.

Also, certain axes are mentioned herein as being orthogonal, such as axes 48 and 58. Although these axes do not necessarily intersect it is to be understood that two axes are considered to be orthogonal if there is a plane containing one of the axes that is orthogonal to the other axis.

Figure 2:
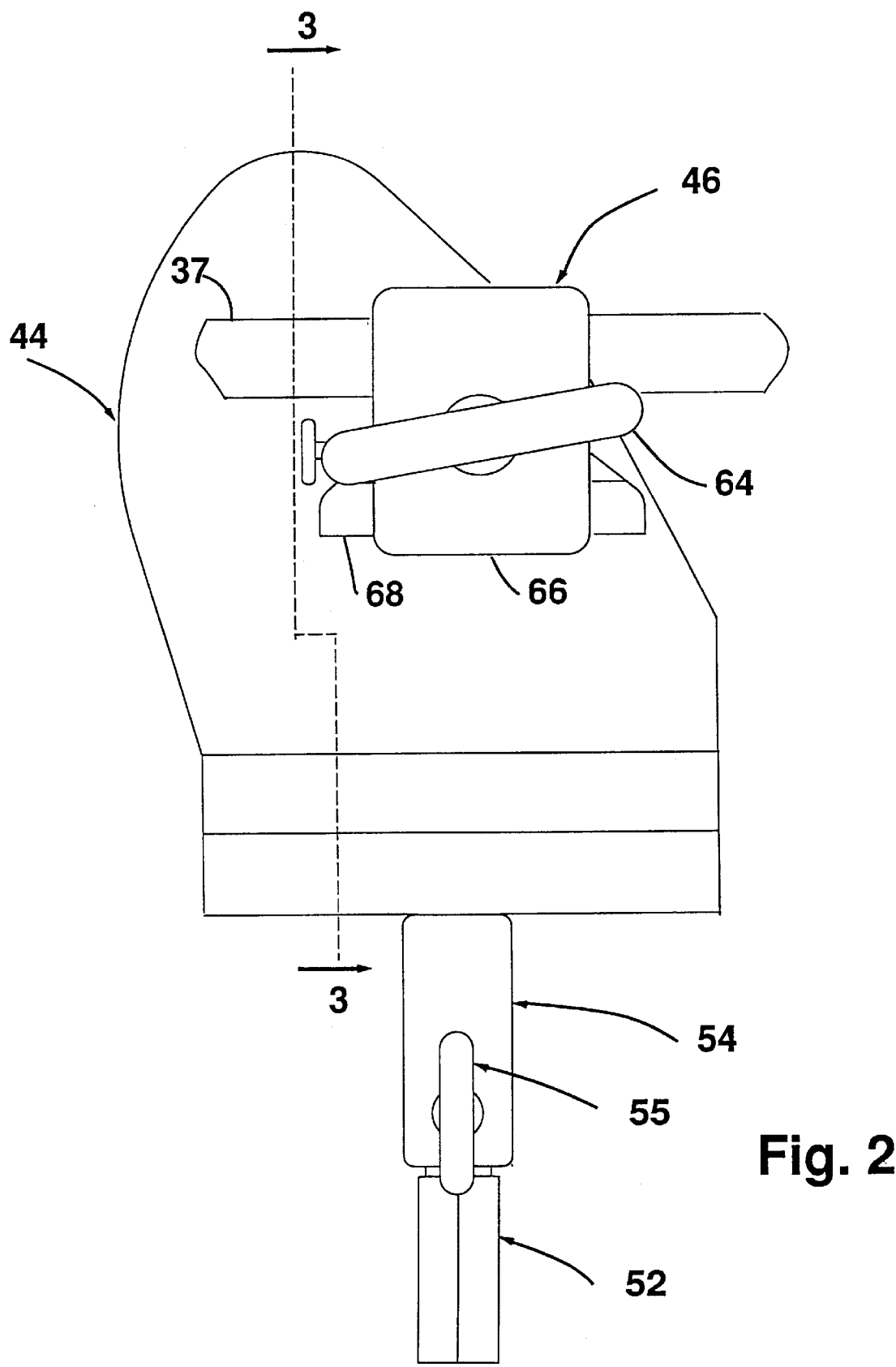
FIG. 2 is a side view of a first pivot assembly of the apparatus of FIG. 1.
Figure 3:
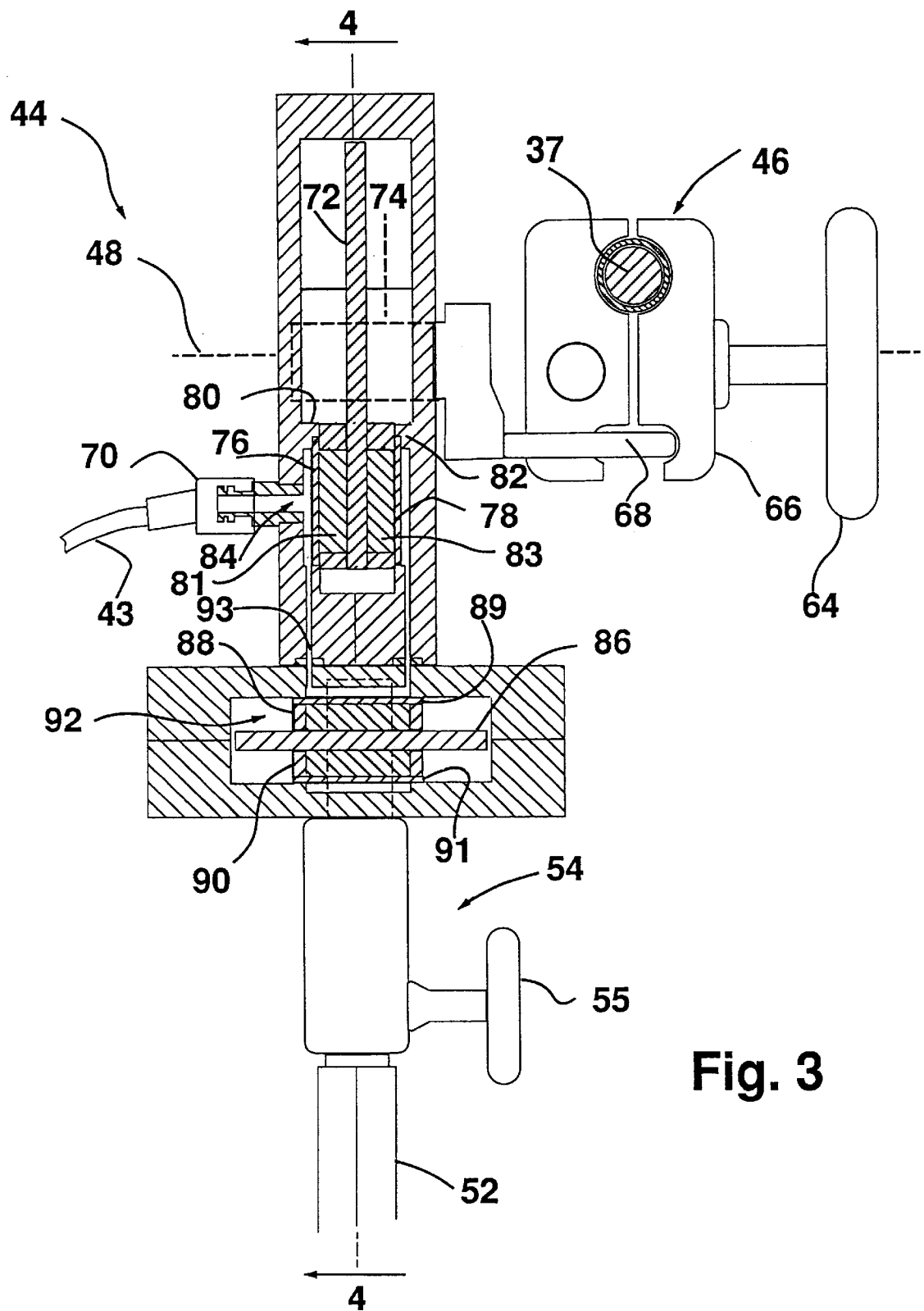
FIG. 3 cross-section taken along line 3—3 of FIG. 2.

FIGS. 2 and 3 show detail of first pivot assembly 44 in side section and end views respectively. A fourth clamp assembly handle 64 secures arm section 37 to clamp assembly 46 and secures clamp assembly 46 to a bracket 68 mounted to a housing 66. Gas outlet line 43 is connected to first pivot assembly 44 at a luer fitting 70. Note that FIGS. 2 and 3 show pivot assembly 44 in a different orientation relative to third clamp assembly 54 than FIG. 1 for purposes of illustration.

Figure 4:
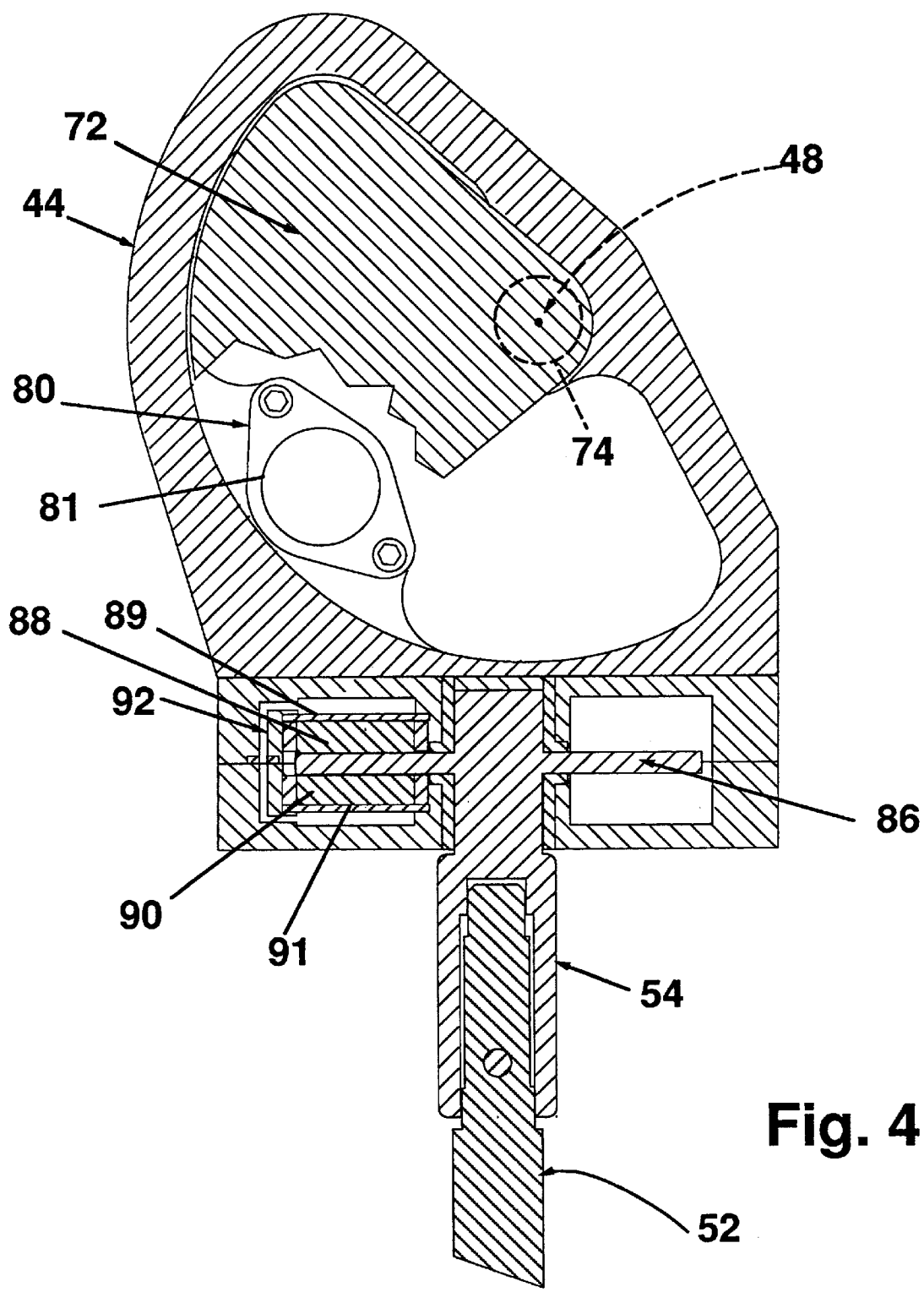
FIG. 4 is a cross-section taken generally along the line 4—4 of FIG. 3 showing the pressurized as operated lock assemblies which lock the horizontal axis pivot and the longitudinal axis arc.

Turning to FIGS. 3 and 4, partial internal detail of first pivot assembly 44 is shown. A horizontal axis main disc 72 pivots about axis 48 on a main shaft 74 which is fixedly attached to main disc 72. Main disc pressure pads 76, 78 are retained by main disc pressure pad retainers 80, 82 respectively, formed in housing 66. Pressure pads 81, 83 frictionally engage main disc 72 when pressurized gas is applied via gas outlet flow line 43 into a first pivot assembly gas chamber 84.

FIGS. 3 and 4 also show detail of the lower section of first pivot assembly 44. A vertical axis main disc 86 is fixedly attached to third clamp assembly 54. Vertical axis pressure pads 88, 90 are frictionally engaged to vertical axis main disc 86 when pressurized gas is applied to vertical axis gas chamber 92 causing pressure by vertical axis gas membranes 89, 91 against pads 88,90 respectively. Pressurized gas is conducted to chamber 92 from chamber 84 via connecting channels, such as channel 93.

Figure 5:
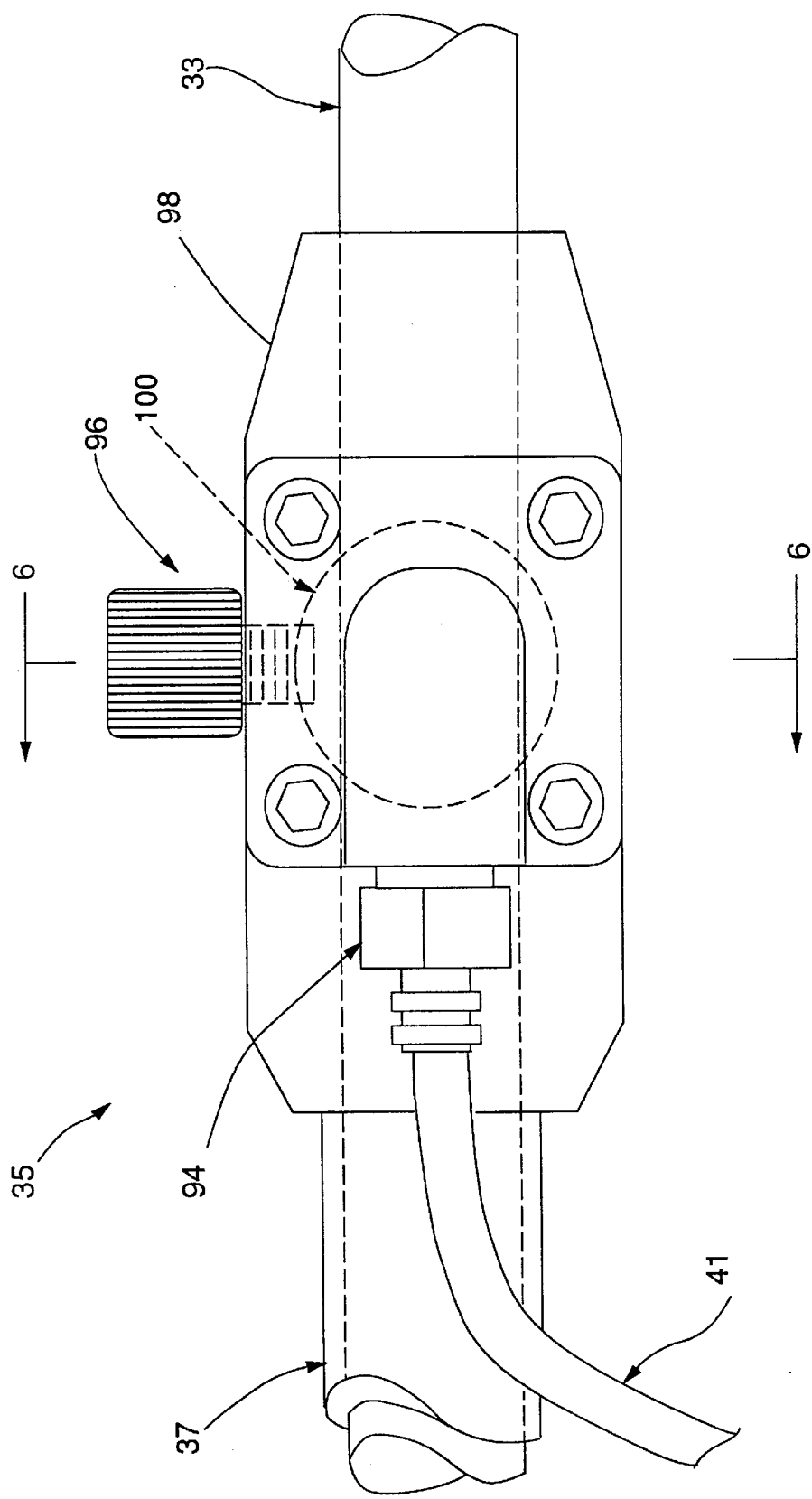
FIG. 5 top view of the arm lock assembly of the apparatus of FIG. 1.
Figure 6:
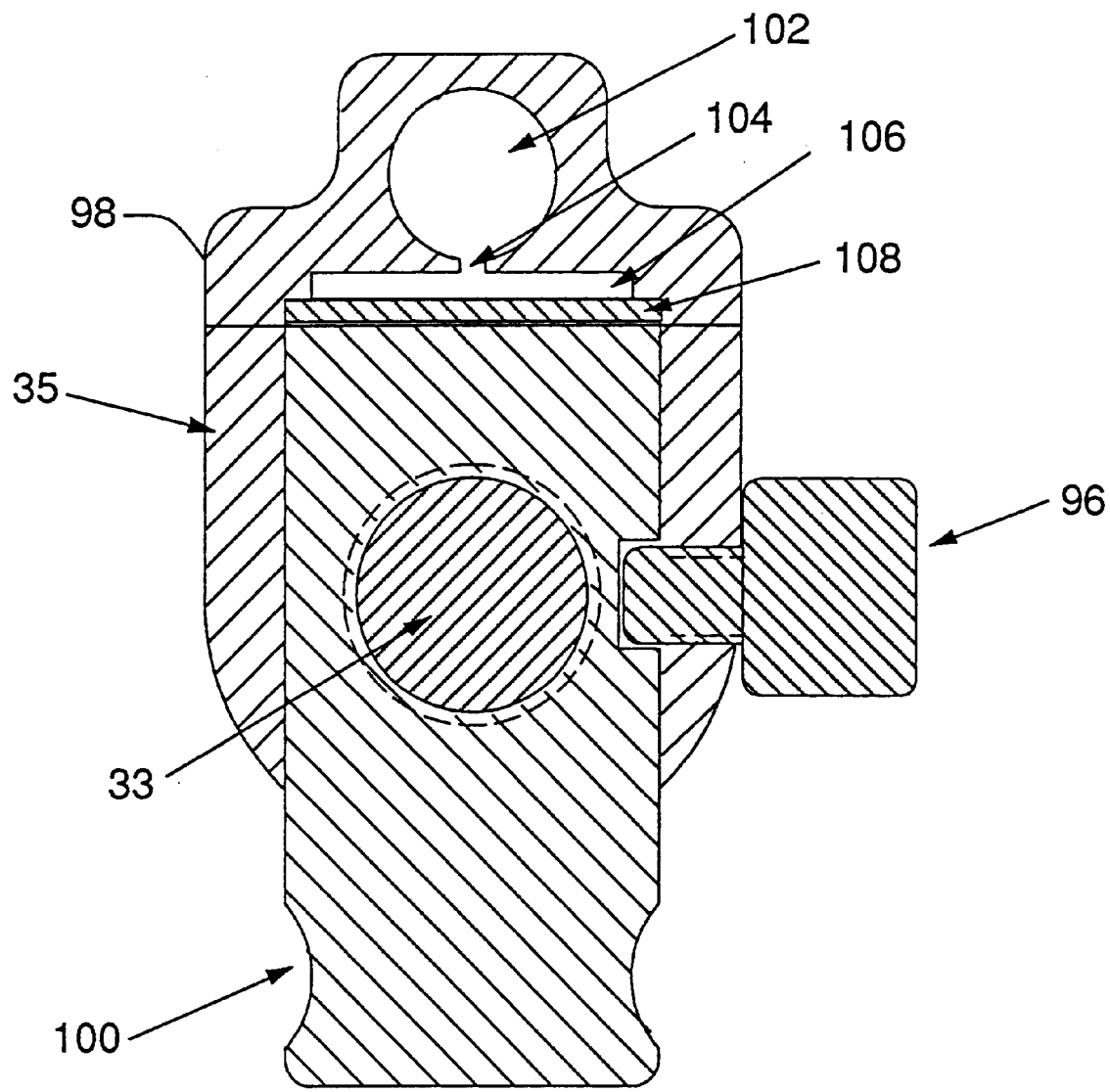
FIG. 6 is a cross-sectional view taken generally along the line 6—6 of FIG. 5 showing detail of the pressurized gas operated lock assembly which locks the telescoping second arm section relative to the first arm section.

FIG. 5 is a top view of arm lock assembly 35. FIG. 6 is a sectional view of lock assembly 35 taken generally along the line 6—6 in FIG. 5. Gas outflow line 41 connects to a lock assembly luer fitting 94. An arm section lock retainer 96 is threadedly received in a bore in an outer housing 98 and extends into an inner rod lock 100. FIG. 6 shows detail of lock assembly gas inlet chamber 102 which communicates via an aperture 104 to a gas cavity 106. When pressurized gas enters gas cavity 106, an arm lock gas membrane 108 frictionally locks second arm section 33 against inner rod lock 100.

Figure 8:
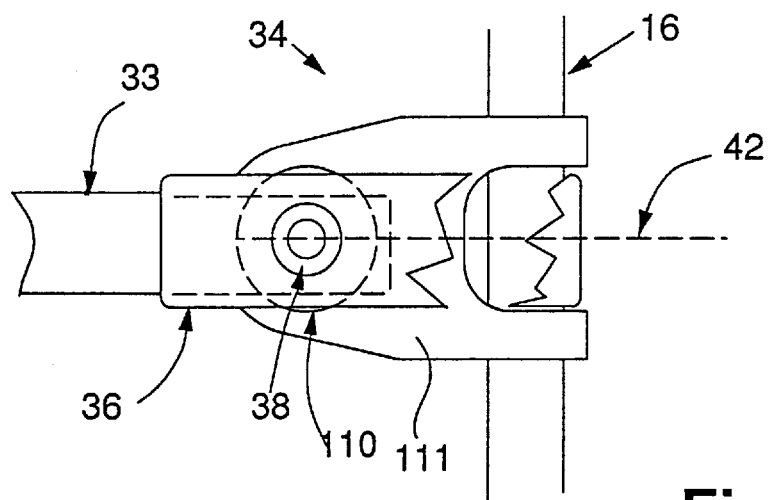
FIG. 8 is a top view of the grip of FIG. 7 shown with the strap partially cut away to show detail of the grip when in operation holding a shaft of an endoscope.
Figure 7:
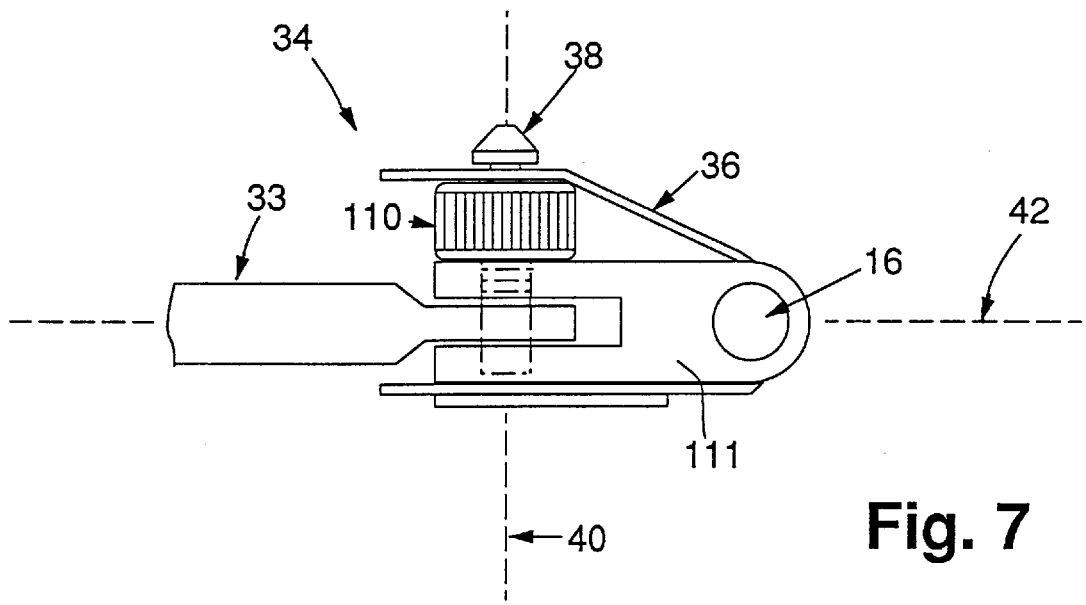
FIG. 7 is a side view of the grip of the apparatus of FIG. 1.

FIGS. 7 and 8 show detail of grip 34 which forms a second pivot assembly 38. A grip retainer 110 is threadedly received in a bore in the wings of a C-shaped clamp element 111 and in the distal end of second arm section 33. Grip 34 is thereby rotatable about grip axis 40 with respect to second arm section 33. Strap 36 frictionally contacts the side of cannula 16 in the opening formed in element 111. As shown, the tips of the C-shaped clamp elements have bores sized for receiving the cannula shaft.

Figure 9:
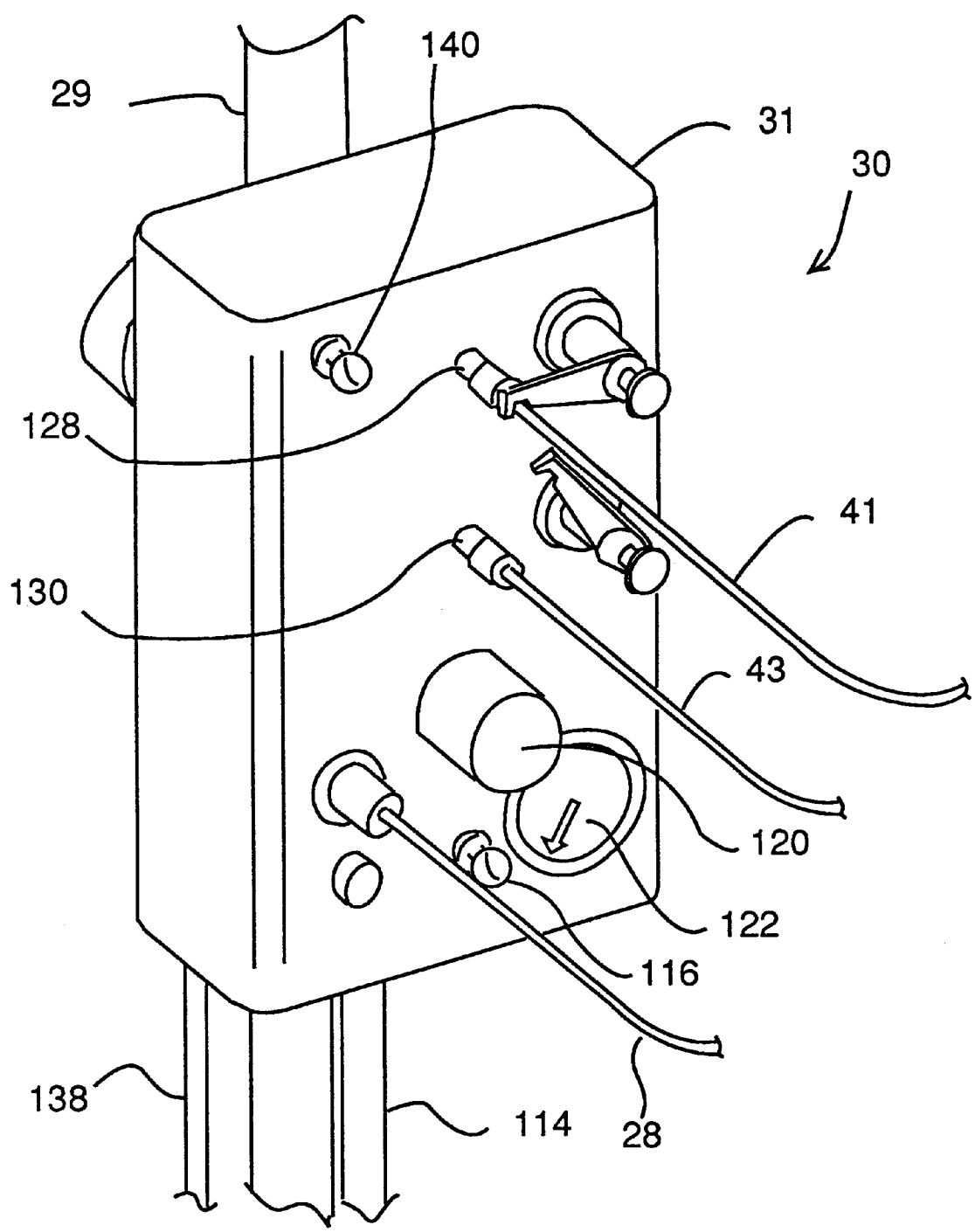
FIG. 9 is in isometric view of the lock control housing shown in FIG. 1.
Figure 10:
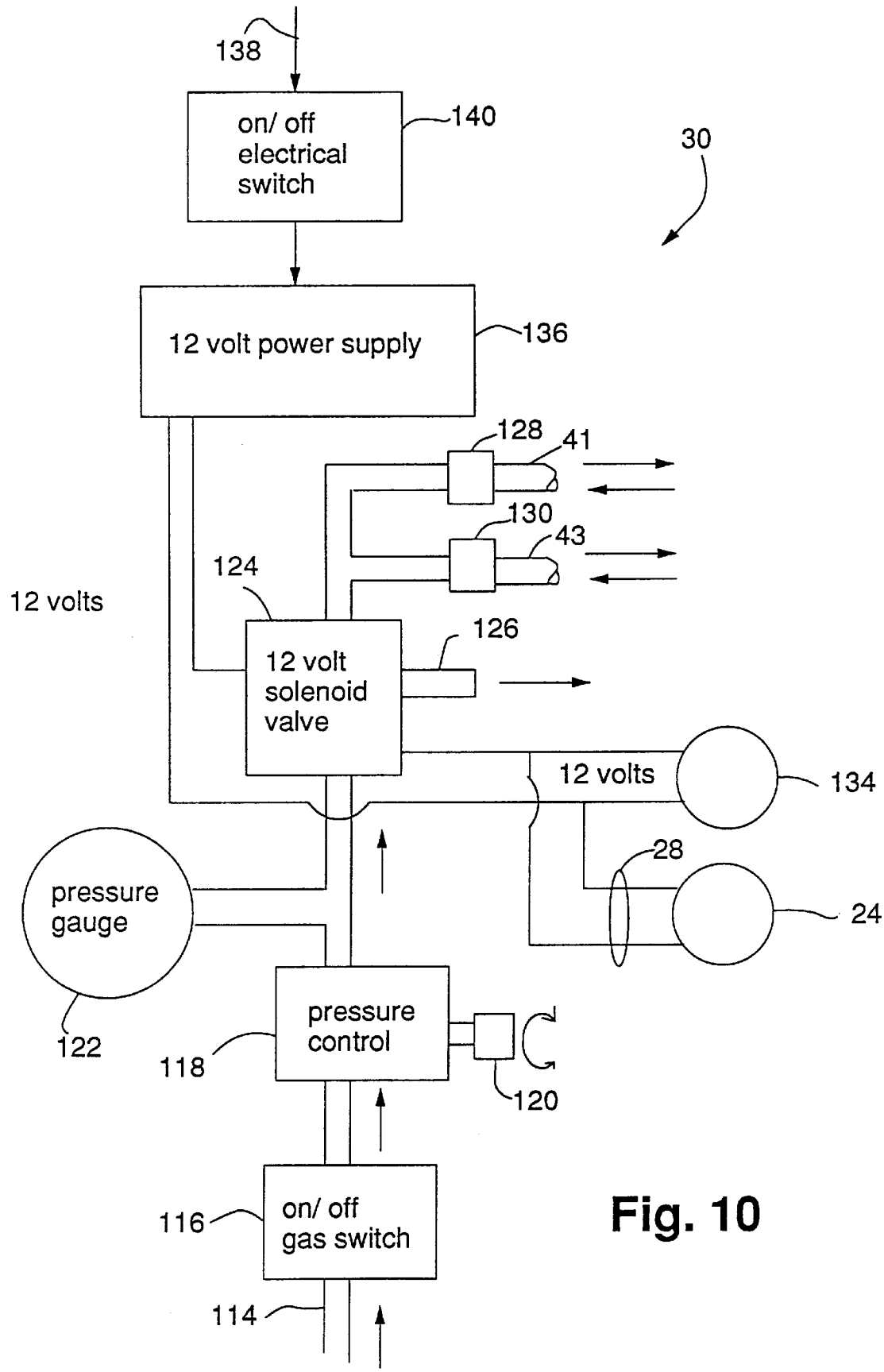
FIG. 10 is a general schematic of the lock control system of the apparatus of FIG. 1.

FIGS. 9–12 show detail of control system 30. FIG. 9 is an isometric view of housing 31 containing many of the components of system 30. FIG. 10 is a general schematic of the control system. Gas is supplied from a standard source through a supply line 114. The pressurized gas passes through a manually operated mechanical gas switch 116 and a control valve 118 manually adjustable by a knob 120 mounted on housing 31. The adjusted pressure is indicated by a gauge 122. The gas then pass through a 12-volt solenoid-operated gas valve 124 and out through gas feed lines 41 and 43 through respective luer fittings 128 and 130. Valve 124 includes a gas vent 126.

Gas valve 124 is manually actuated by remote electrical switch 24 mounted on the laparoscope camera, as shown in FIG. 1, or by a resident switch 134 mounted on housing 31. The preferred solenoid operates on a 12 volt direct current (DC) supply provided by a 12-volt power supply 136 that is preferably a converter connected to a conventional 110 volt alternating current (AC) supply fed on an electrical line 138. Input electrical power is controlled by an on/off switch 140.

Figure 11:
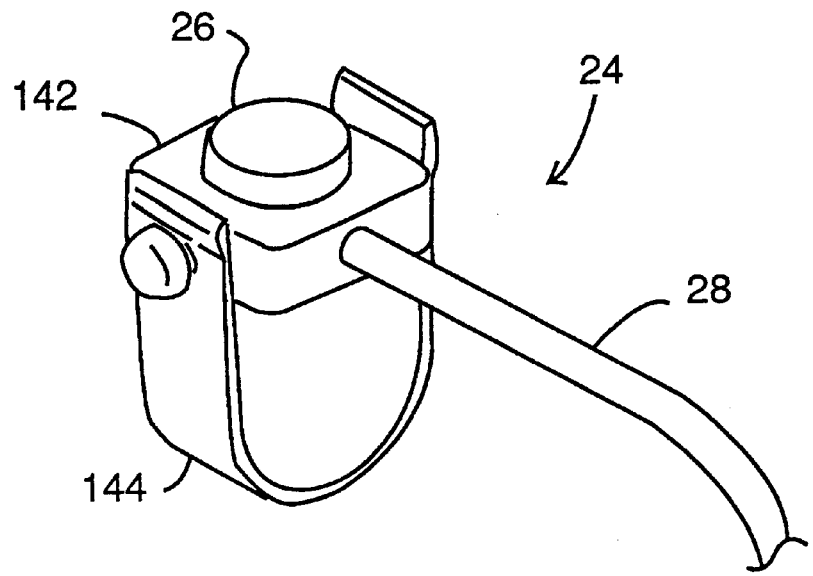
FIG. 11 is a isometric view of the lock actuating control switch of the apparatus of FIG. 1.
Figure 12:
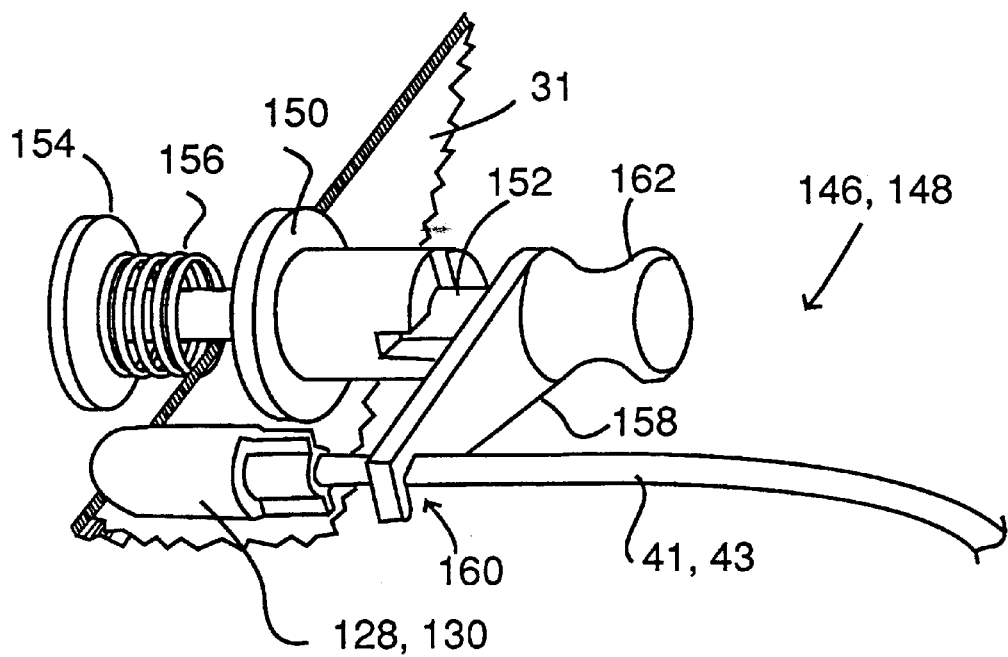
FIG. 12 is an exploded view of a gas line safety mounted on the lock control housing shown in FIG. 9.

Remote gas control switch 24 is shown enlarged in FIG. 11. Control button 26, also referred to as a lever, is mounted on a switch housing 142, operates a conventional "momentary on" switch, not shown. Housing 142 is supported on camera 20 by a silicone strap 144.

Control housing 31 also has attached to it gas line safeties 146 and 148. One safety is associated with each luer connection for outflow lines 41 and 43. The gas outflow lines preferably have male luer connectors at each end, and both lines are the same length so that they are interchangeable. The safeties are also the same and are shown enlarged in FIG. 12. Each safety includes a base 150 mounted to housing 31 and having a central bore through which a shaft 152 passes. An end of the shaft extends internally of housing 31 and has a broad flange or plate 154 mounted on it. Shaft 152 extends through a compression spring 156 captured between plate 154 and housing 31. Spring 156 urges plate 154 and shaft 152 inwardly. Attached to the outer end of the shaft is an elongate arm 158 having a recess 160 sized for receiving a gas flow tube 41 or 43. Positioning of arm 158 is manually controlled by a knob 162 also positioned on the outer end of shaft 152. After luer fitting 128 or 130 is connected to the corresponding fitting mounted on housing 31, knob 162 is pulled outwardly until arm 158 is beyond the luer fitting and rotated so that gas line 41 or 43 is received in recess 160. The knob is then released, allowing the end of arm 158 to press inwardly on the luer fitting. The force of spring 156 keeps the luer fittings from coming loose in the event they are not securely connected.

Figure 13:
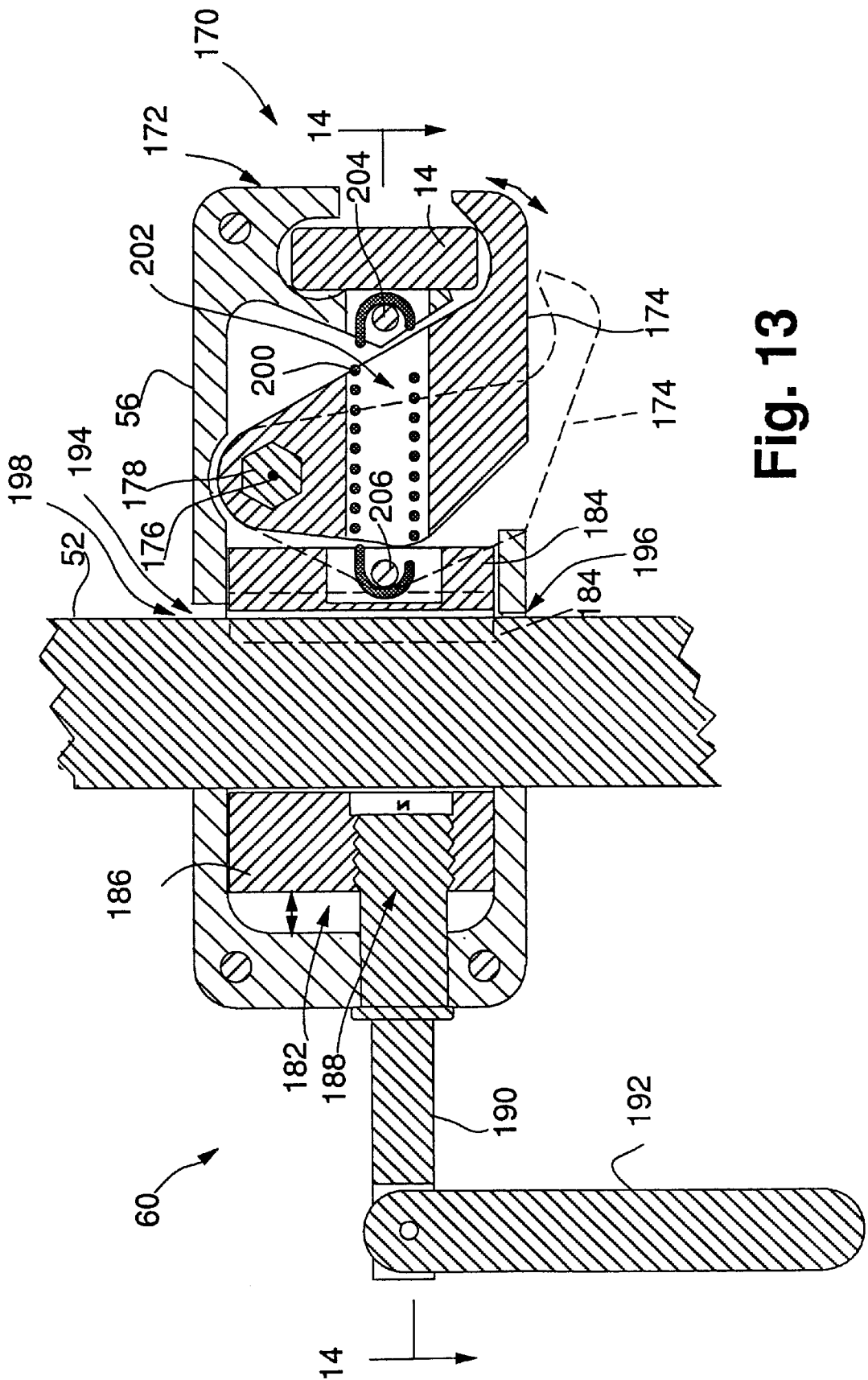
FIG. 13 is a vertical cross-section of the base clamp assembly shown in FIG. 1.
Figure 14:
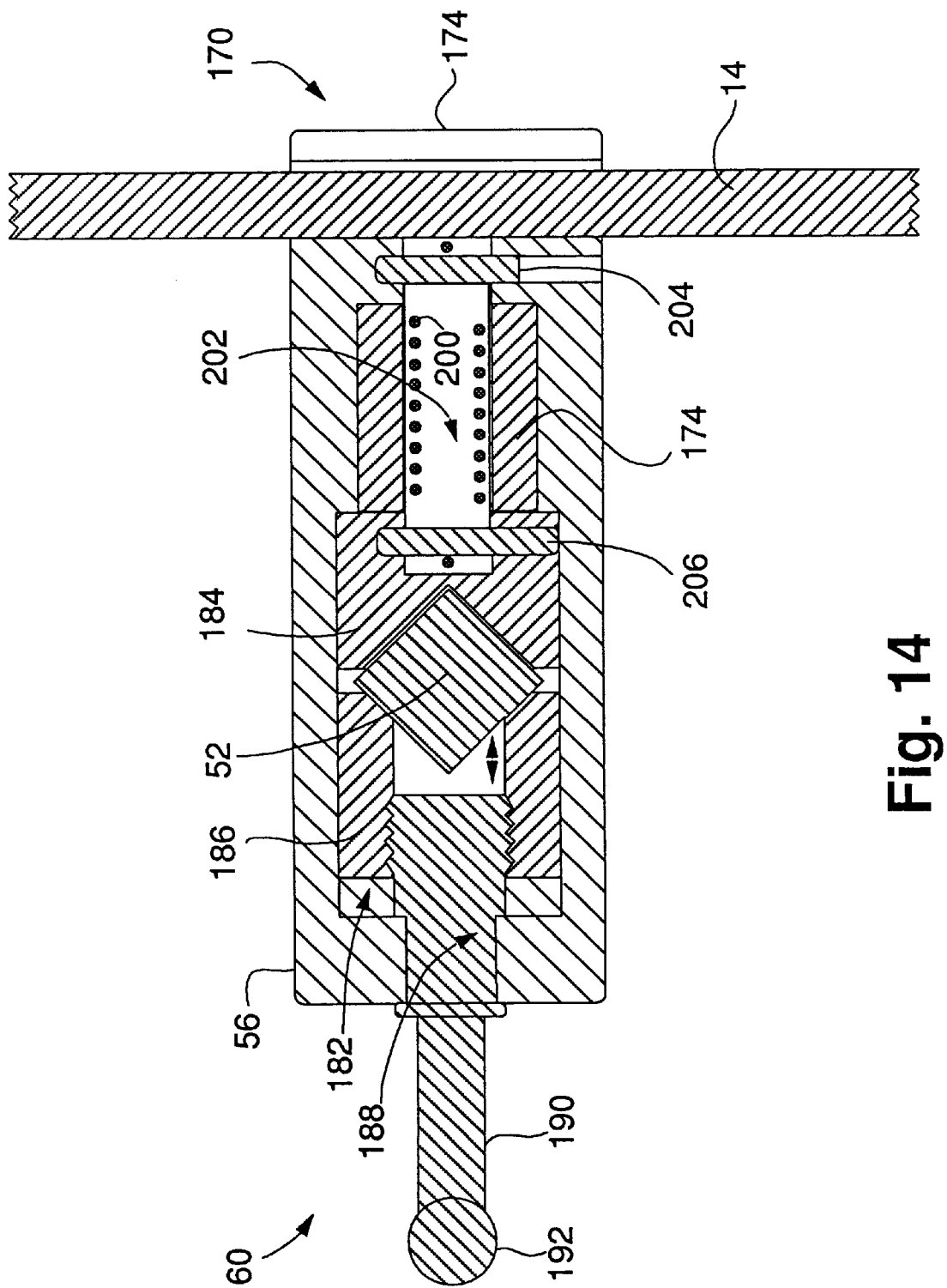
FIG. 14 is a cross-section taken along line 14—14 in FIG. 13.

Referring now to FIGS. 13 and 14, the preferred structure for base clamp assembly 60 is shown. Clamp assembly 60 is dual-acting in the sense that it provides clamping of base 56 onto rail 14 and also secures shank 52 to the base, and thereby to the rail. As shown particularly in FIG. 13, clamp assembly 56 includes a rail clamp 170 for securing base 56 to rail 14. Clamp 170 includes an upper jaw 172 integrally formed in base 56, which base is a housing for the clamp assembly. The rail clamp also includes a movable lower jaw 174 that pivots about an axis 176 defined by an axle 178. Movement of jaw 174 about axis 176 is controlled by a release handle 180 attached to axle 178 and positioned outside of base 56, as shown particularly in FIG. 1.

Base 56 defines an internal channel 182 supporting inner and outer shank jaws 184 and 186. The surfaces of jaws 184 and 186 are beveled to mate with corresponding faces of shank 52, as shown in FIG. 14. Outer jaw 186 has a threaded bore, shown generally at 188, in which is threadedly received a threaded shaft 190 attached to a clamp handle 192. Outer jaw 186 is moved toward and away from inner jaw 184 by rotation of handle 192.

Base 56 has upper and lower openings 194 and 196. also referred to as a keyway 198, sized larger than shank 52 so that the shank can be positioned freely in between jaws 184 and 186. Further, as will be seen, during tightening of the shank in base 56, jaw 184 moves toward rail clamp 170 as lower rail jaw 174 pivots. The openings in the base are sized sufficiently large to accommodate the corresponding migration of shank 52 in base 56 during tightening of the base clamp assembly.

It is also seen that a compression spring 200 extends through a bore 202 in lower jaw 174. The ends of the spring are anchored by a pin 204 secured in housing 56 and a pin 206 secured in inner jaw 184. Spring 200 urges inner shank jaw 184 against lower rail jaw 174, and thereby urging rail clamp 170 toward a closed position.

During setup of the scope holder, base clamp assembly 60 is attached to rail 14 before shank 52 is put into keyway 198. Release handle 180 is pivoted upwardly as shown in FIG. 1. This causes jaw 174 to pivot downwardly, as shown in FIG. 13, opening the jaws of rail clamp 170. Inner shank jaw 184 moves outwardly in channel 182, toward outer jaw 186, as shown by the dashed outline of jaw 184 in FIG. 13. The rail clamp is positioned over the rail and the release handle is released. Spring 200 urges the rail clamp closed, temporarily securing the base clamp assembly on the rail.

With lower jaw 174 in a closed position, spring 200 has pulled inner shank jaw 184 away from outer jaw 186, creating enough of an opening between them to freely receive shank 52. Shank 52, now attached to pivot assembly 44, is inserted into keyway 198 in any one of the four rotational positions of the shank. The height of the pivot assembly is set so that the arm assembly will clear the patient and have the range of movement required for the procedure. The clamp handle 192 is tightened. This drives outer jaw 186 against shank 52, which is thereby pressed against inner jaw 184. Jaw 184 correspondingly presses against lower rail jaw 174, causing it to pivot about axis 176, further tightening rail clamp 170. It is thus seen that a single action of tightening clamp handle 192 secures both the shank and the rail in the base clamp assembly. By loosening the clamp handle, the shank can be moved up or down. In order to reposition the base along the rail, the release handle must also be raised to provide a slight amount of clearance between the rail and the rail jaws.

When first pivot assembly 44 is secured to the upper end of shank 52 by third clamp assembly 54, arm section 37 is then inserted into fourth clamp assembly 46 and secured by tightening fourth clamp assembly handle 64. Second arm section 33 is inserted into arm lock assembly 35 and held in place by second arm assembly lock retainer screw 96.

Grip 34 is attached to the exposed end of second arm section 33. A cannula 16 is installed in the grip and strap 36 is connected to grip 34 as shown.

Gas control housing 31 is attached to a pole 29, the AC cord is plugged into an electrical outlet and pressure gas source line 114 is attached to a source of nitrogen gas having a pressure of 100 to 150 pounds. Electrical switch 140 and mechanical gas switch 126 are turned on. Alternate gas flow control button 134 is then depressed to prevent gas form escaping from the two luer fittings. While holding the alternate control button, the pressure control knob is rotated to set the pressure at between 100 and 150 psi. The gas is then turned off until both ends of both gas outflow lines 41 and 43 have been connected. Control switch 24 is connected to camera 20. Light line 22 is connected to endoscope equipment according to procedures appropriate to the particular equipment being used.

Once apparatus 10 is assembled, cannula 16 may be positioned as desired by grasping control 24 and endoscope 12. By depressing button 26, freedom of motion is provided about vertical axis 58, horizontal axis 48, longitudinal axis 42 and along longitudinal axis 42. Due to residual friction at the various gas operated locking assemblies and support of the endoscope by the user, apparatus 10 does not collapse while button 26 is closed. When button 26 is released, the entire apparatus is held firmly in the position selected at the moment the button was released.

Variations in form and detail may be made in the preferred embodiment of the present invention without varying from the spirit and scope of the invention as defined in the claims when construed according to applicable legal principles. For instance, the pressurized gas operation described with reference to the preferred embodiment could be replaced with a negative air pressure system or a computer controlled system employing air or electricity driven servo motors. Other mechanical linkage configurations could be designed which would provide different geometry of the apparatus such as an arm of different length or different degrees of motion about the various axes. Further, apparatus 10 is shown designed for ease of assembly and disassembly. Other designs would provide the same functionality. The preferred embodiment is thus provided for purposes of explanation and illustration, but not limitation.

The invention claimed is:

1. An instrument support apparatus for supporting an instrument having a shaft extending along a shaft axis relative to a patient positioned adjacent to an external frame comprising:

a base fixedly mountable onto an external frame;

a grip defining a support axis and mountable to an instrument for supporting the instrument with the shaft axis extending along the support axis;

a first pivot assembly mounted relative to the base providing pivoting about first and second orthogonal axes;

an arm assembly having a longitudinal axis and having a first end mounted relative to the first pivot assembly and a second end movable along and about the longitudinal axis;

a second pivot assembly mounting the grip to the second end of the arm assembly, the grip being pivotable relative to the second end of the arm assembly about a grip axis perpendicular to the longitudinal axis of the arm and perpendicular to the support axis;

whereby the grip is pivotable about a point on the support axis spaced from the grip.

2. An instrument support apparatus according to claim 1 further comprising:

a first lock assembly remotely actuatable for locking the first pivot assembly, and thereby preventing movement of the grip about the first and second axes; and a second lock assembly, also remotely actuatable, for locking the arm assembly, and thereby preventing movement of the grip along and about the longitudinal axis of the arm assembly;

whereby, when the first and second lock assemblies are actuated, the grip is immovable about the first and second axes, and is immovable about and along the longitudinal axis of the arm.

3. An instrument support apparatus according to claim 2 further comprising:

a manually operable lock actuating controller coupled to the first and second lock assemblies for controlling actuation of the first and second lock assemblies concurrently.

4. An instrument support apparatus according to claim 3 wherein the first and second lock assemblies are actuated by pressurized gas, and the controller controls the flow of the pressurized gas to the first and second lock assemblies, the controller further comprising a vent for venting gas from the first and second lock assemblies during deactuation of the first and second lock assemblies.

5. An instrument support apparatus according to claim 4 wherein the controller further comprises a normally open gas valve operable for actuating the first and second lock assemblies when in the open position and deactuating the first and second lock assemblies when in a closed position.

6. An instrument support apparatus according to claim 5 wherein the controller further comprises a manually operable lever coupled to the gas valve for closing the gas valve when the lever is operated, the lever being adapted for mounting onto the instrument whereby the user may control the gas valve with the same hand that is positioning the instrument.

7. An instrument support apparatus according to claim 1 wherein the position of the first pivot assembly is adjustable relative to the base.

8. An instrument support apparatus according to claim 1 wherein the first pivot assembly provides pivoting about only the first and second axes.

9. An instrument support apparatus according to claim 1 wherein the arm assembly includes a first arm section having the first end and a second arm section having the second end, with the second arm section being movable along the longitudinal axis relative to the first arm section.

10. An instrument support apparatus according to claim 1 wherein the grip comprises a generally C-shaped clamp for receiving an instrument shaft and a strap matingly encompassing the C-shaped clamp for securing an instrument shaft in the C-shaped clamp.

11. An instrument support apparatus according to claim 1 wherein the position of the first end of the arm assembly is adjustable along the longitudinal axis relative to the first pivot assembly.

12. An instrument support apparatus according to claim 11 further comprising a clamp for securing the first arm end relative to the first pivot assembly.

13. An instrument support apparatus according to claim 1 wherein the longitudinal axis is perpendicular to the second axis.

14. An instrument support apparatus according to claim 13 further comprising;
   a first lock assembly remote actuatable for locking the first pivot assembly and thereby preventing movement of the grip about the first and second axis; and
   a second lock assembly, also remotely actuatable, for locking the second end of the arm assembly relative to the first end of the arm assembly and thereby preventing movement of the grip along and about the longitudinal axis of the arm assembly.
   whereby, when the first and second lock assemblies are actuated, the grip is immovable about the first and second axes, and is immovable about and along the longitudinal axis of the arm assembly.

15. An instrument support apparatus for supporting an instrument having a shaft extending along a shaft axis relative to a patient positioned adjacent to an external frame comprising:
   a base fixedly mountable on the external frame;
   a shank defining a vertical shank axis and mated to and insertable in the base and adjustable to a plurality of vertical positions relative to the base;
   first and second clamp assemblies, the second clamp assembly defining a horizontal axis and being adjustable through an arc in a plane perpendicular to the horizontal axis;
   a first pivot assembly mounted atop the shank and secured thereto by the first clamp assembly, and rotatable about the shank axis
   an arm assembly defining a longitudinal axis perpendicular to the horizontal axis and having a first arm section mounted in the second clamp assembly and adjustable along the longitudinal axis relative to the first pivot assembly and a second arm section movable along the longitudinal axis relative to the first arm section, the second arm section also being rotatable about the longitudinal axis;
   a grip having a grip axis perpendicular to the longitudinal axis, a generally C-shaped clamp for clamping the instrument relative to the second arm section and a strap matingly encompassing the C-shaped clamp, the C-shaped clamp and the strap being secured to the second arm section and defining the grip axis, the C-shaped clamp further having a bore for containing the instrument shaft;
   a second pivot assembly mounting the grip to the second arm section of the arm assembly for pivoting the grip relative to the second arm section about a grip axis perpendicular to the longitudinal axis of the arm assembly and perpendicular to the support axis;
   a first pressurized-gas-actuated lock assembly for locking the first pivot assembly on the shank axis and for locking the third clamp assembly;
   a second pressurized-gas-actuated lock assembly for locking the second arm section relative to the first arm section both along the longitudinal axis and rotationally; and
   a manually operable lock-actuating controller, coupled to the first and second lock assemblies for actuating the lock assemblies simultaneously when in a first operating state and releasing the first and second lock assemblies when the controller is in a second operating state, the controller having a vent for venting gas from the first and second lock assemblies when in the second operating state and a lever adapted for mounting onto the instrument for controlling operation of the controller by a user by the same hand that is positioning the instrument;
   whereby the grip is movable by a user using only one hand.

* * * * *